United States Patent
Blanz et al.

(10) Patent No.: US 7,126,332 B2
(45) Date of Patent: Oct. 24, 2006

(54) DOWNHOLE HIGH RESOLUTION NMR SPECTROSCOPY WITH POLARIZATION ENHANCEMENT

(75) Inventors: Martin Blanz, Celle (DE); Thomas Kruspe, Wienhausen (DE)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/696,995

(22) Filed: Oct. 30, 2003

(65) Prior Publication Data

US 2004/0119471 A1 Jun. 24, 2004

Related U.S. Application Data

(63) Continuation-in-part of application No. 10/404,408, filed on Apr. 1, 2003, which is a continuation-in-part of application No. 09/910,209, filed on Jul. 20, 2001, now Pat. No. 6,609,568.

(60) Provisional application No. 60/406,082, filed on Aug. 26, 2002, provisional application No. 60/369,268, filed on Apr. 2, 2002.

(51) Int. Cl.
G01V 3/00 (2006.01)

(52) U.S. Cl. ........................... 324/303; 324/300

(58) Field of Classification Search ................ 324/303, 324/300, 304, 307, 309, 318; 600/420
See application file for complete search history.

(56) References Cited

U.S. PATENT DOCUMENTS

| | | | |
|---|---|---|---|
| 3,096,476 A * | 7/1963 | Poindexter et al. ......... | 324/303 |
| 3,258,681 A * | 6/1966 | Brown et al. ............... | 324/303 |
| 3,321,965 A | 5/1967 | Johnson et al. ............. | 73/155 |
| 3,500,176 A * | 3/1970 | Kastler et al. .............. | 324/304 |
| 4,964,101 A | 10/1990 | Liu et al. ..................... | 367/31 |
| 5,233,866 A | 8/1993 | Desbrandes ................. | 73/155 |
| 5,306,640 A | 4/1994 | Vinegar et al. .............. | 436/29 |
| 5,703,286 A | 12/1997 | Proett et al. ............. | 73/152.05 |
| 5,708,204 A | 1/1998 | Kasap .................... | 73/152.52 |
| 5,803,186 A | 9/1998 | Berger et al. ................ | 175/50 |
| 5,812,068 A | 9/1998 | Wisler et al. ............ | 340/855.5 |
| 5,827,501 A | 10/1998 | Jørgensen et al. ......... | 424/9.33 |
| 5,936,405 A | 8/1999 | Prammer et al. ........... | 324/303 |
| 6,111,408 A | 8/2000 | Blades et al. ............... | 324/303 |
| 6,111,409 A | 8/2000 | Edwards et al. ............ | 324/303 |
| 6,147,490 A * | 11/2000 | Watanabe ................... | 324/307 |
| 6,184,683 B1 * | 2/2001 | Emsley et al. .............. | 324/309 |

(Continued)

FOREIGN PATENT DOCUMENTS

EP 0490421 A1 6/1992

(Continued)

OTHER PUBLICATIONS

Boyd M. Goodson; *Nuclear Magnetic Resonance of Laser-Polarized Nobel Gases in Molecules, Materials, and Organisms*, Journal of Magnetic Resonance 155, 157-216 (2002), pp. 157-216, 39 Figs.

*Primary Examiner*—Brij B. Shrivastav
(74) *Attorney, Agent, or Firm*—Madan, Mossman & Sriram, P.C.

(57) ABSTRACT

An apparatus and method is discussed for characterizing a fluid sample downhole of aliphatic hydrocarbon compounds, aromatic hydrocarbon compound, or connate mud filtrates containing carbon-13 isotopes using an enhanced nuclear magnetic resonance (NMR) signal on a measurement-while-drilling device. To enhance the carbon-13 NMR signal these nuclei are being hyperpolarized. Either the Overhauser Effect (OE) or the Nuclear Overhauser Effect or optical pumping and the Spin Polarization Induced Nuclear Overhauser Effect (SPINOE) can serve as a mechanism for hyperpolarization of the carbon-13 nuclei.

53 Claims, 10 Drawing Sheets

U.S. PATENT DOCUMENTS

| | | | |
|---|---|---|---|
| 6,294,914 B1 * | 9/2001 | Fiat | 324/312 |
| 6,346,813 B1 | 2/2002 | Kleinberg | 324/303 |
| 6,426,058 B1 * | 7/2002 | Pines et al. | 424/9.3 |
| 6,453,188 B1 * | 9/2002 | Ardenkjaer-Larsen et al. | 600/420 |
| 6,815,950 B1 * | 11/2004 | Speier | 324/303 |
| 6,818,202 B1 * | 11/2004 | Pines et al. | 424/9.3 |
| 6,958,604 B1 | 10/2005 | An et al. | 324/303 |

FOREIGN PATENT DOCUMENTS

| | | |
|---|---|---|
| EP | 0520903 A2 | 12/1992 |
| EP | 0698722 A2 | 2/1996 |
| EP | 0698722 A3 | 2/1996 |
| EP | 0698722 A3 | 6/1997 |

* cited by examiner

THERMAL EQUILIBRIUM

FORCED EQUILIBRIUM

DOWNHOLE HIGH RESOLUTION NMR SPECTROSCOPY WITH POLARIZATION ENHANCEMENT

CROSS REFERENCE TO RELATED APPLICATIONS

This patent application is a continuation-in-part of and claims priority from U.S. patent application Ser. No. 10/404,408, entitled "A Method and Apparatus for Combined NMR and Formation Testing For Assessing Relative Permeability with Formation Testing and Nuclear Magnetic Resonance Testing", by Georgi, et al filed on Apr. 1, 2003, which is incorporated herein by reference in its entirety, and which is a continuation-in-part of and claims priority from U.S. patent application Ser. No. 09/910,209 entitled "Apparatus and Method for In Situ Analysis of Formation Fluids" by Krueger et al., filed on Jul. 20, 2001 now U.S. Pat. No. 6,609,568, which is incorporated herein by reference in its entirety. U.S. patent application Ser. No. 10/404,408 claims priority from U.S. patent application Ser. No. 60/369,268 entitled, "Combined NMR and Formation Testing" by Georgi et al. filed on Apr. 2, 2002, and claims priority from U.S. patent application Ser. No. 60/406,082 filed Aug. 26, 2002 entitled, "A Method and Apparatus for Combined NMR and Formation Testing For Assessing Relative Permeability with Formation Testing and Nuclear Magnetic Resonance Testing" by Georgi et al.

BACKGROUND OF THE INVENTION

1. Field of the Invention

The present invention is related to the field of downhole nuclear magnetic resonance (NMR) investigation of wellbore fluids. In particular, the invention relates to methods for increasing NMR signal amplitudes in measurements of fluids in downhole environments.

2. Description of the Related Art

Performing measurements on fluid samples is desirable in many oil industry applications. In the prior art, such measurements are typically made by bringing samples to the surface using sealed containers and sending the samples for laboratory measurements. A number of technical and practical limitations are associated with this approach. Such limitations include the limited sample material extractable from a limited number of downhole locations. Also, samples undergo reversible and irreversible changes as a result of the temperature and/or pressure changes while being brought to the surface and during transportation. For example, gases come out of solution, waxes precipitate, and asphaltenes chemically recombine. Irreversible changes eliminate the possibility of ever determining actual in situ fluid properties. Reversible changes are deleterious because they occur slowly and therefore impact sample handling and measurement efficiency. Furthermore, since fluid analysis laboratories are frequently distant from the well site, there are substantial delays—often several weeks—in obtaining results. If a sample is for some reason corrupted or lost during sampling, transportation, or measurement, there is no possibility of returning to the well to replace it.

In view of the foregoing, various methods exist for performing downhole measurements of petrophysical parameters of a geologic formation. Nuclear magnetic resonance (NMR) logging is among the most important methods which have been developed for a rapid determination of such parameters, including formation porosity, composition of the formation fluid, the quantity of movable fluid, permeability and others. At least in part this is due to the fact that NMR measurements are environmentally safe and are unaffected by variations in the matrix mineralogy. In a typical NMR run, a logging tool is lowered into a drilled borehole to measure properties of the geologic formation near the tool. The tool is pulled up at a known rate and measurements are continuously taken and recorded in a computer memory, so that at the end of the run a complete log is generated showing the properties of the geologic formation along the length of the borehole. Alternatively, NMR logging can be done while the borehole is being drilled.

NMR logging is based on the observation that when an assembly of nuclear magnetic moments, such as those of hydrogen nuclei, are exposed to a static magnetic field, they tend to align along the direction of the magnetic field, resulting in a bulk magnetization. The rate at which equilibrium is established in such bulk magnetization upon provision of a static magnetic field is characterized by the parameter $T_1$, known as the spin-lattice relaxation time. Spin-lattice relaxation is caused by energy transfer between the nuclei and the lattice. Another related and frequently used NMR logging parameter is known as the spin-spin relaxation time (also known as transverse relaxation time) $T_2$. Spin-spin relaxation is caused by flip flop processes of neighboring spins. This results in gradual loss of phase coherence of the magnetic moments and hence in a loss of macroscopic magnetization and hence in a loss of NMR signal. Radiofrequency magnetic field bursts (known as "RF pulses") are used to turn the macroscopic magnetization and to initiate NMR relaxation (see below). It is possible by a succession of RF pulses to generate so-called spin echoes. In fact it is possible to generate with a so-called CPMG sequence of pulses a sequence of spin echoes that decay with the spin-spin relaxation time $T_2$. The NMR echo amplitude of the begin of a CPMG sequence relates directly to the porosity of the earth formation (matrix independent), while both relaxation times provide indirect information about the composition and quantity of the formation fluid, the pore size distribution, and others.

It is not possible to generate a highly homogeneous magnetic field inside the earth formation. For this reason only the NMR signal strength and relaxation can be derived from NMR in the earth formation. There is a need to obtain information about the composition of formation liquids. Formation liquid can be extracted from the formation and analyzed inside the WL or LWD tool in an NMR spectrometer. In this NMR spectrometer the formation liquid sample is NMR-analyzed inside a magnet with comparatively high magnetic field and high magnetic field homogeneity. These magnetic field properties allow chemical shift NMR analysis, not feasible in the formation in situ. Details of this NMR analysis follow in subsequent paragraphs.

The RF frequency $f_0$ needs to meet the NMR resonance condition: $f_0 = \gamma B_0$, where $\gamma$ is the gyromagnetic ratio, a nuclear property specific to the kind of nucleus, and $B_0$ is the externally applied magnetic flux density. A single RF pulse tilts the macroscopic (nuclear) magnetization. The higher the pulse amplitude and the longer the pulse the more will the initial equilibrium magnetization rotate away from the $B_0$ direction. A so-called 90° or $\pi/2$ pulse tilts the magnetization from the direction of $B_0$ to a direction perpendicular to $B_0$. After such a pulse the nuclear magnetization precesses with the nuclear resonance frequency $f_0 = \gamma B_0$ in a plane perpendicular to the $B_0$ vector. The precessing macroscopic magnetization induces a voltage in the NMR sensor coil, the free induction decay (FID). This NMR signal can be analyzed for frequency distribution. This is done, e.g. by executing a Fourier transformation (FT) of the FID, which will yield a frequency spectrum. In general, any known method to convert time-domain data into a frequency spectrum can be used as an alternative to a FT. If the $B_0$ field homogeneity is sufficient, we will find that the frequency spectrum of an NMR signal of a liquid possesses a fine structure. This is caused by the so-called chemical shift that is caused by electrons. The chemical shift depends on the chemical environment of the nucleus. For this reason "Chemical-shift NMR" also called "High-resolution NMR" has been used for a very long time in laboratory NMR for chemical analysis. Alternatively, Continuous Wave NMR (CW NMR) may be used instead of the pulsed NMR just described. CW NMR sweeps either the magnetic field or the RF frequency over the NMR resonance region observing increased RF absorption at the NMR resonances. This way a frequency spectrum is directly acquired without the need for a Fourier transform. (CW NMR got somewhat out of fashion when the Fast Fourier Transform (FFT) algorithm and powerful digital processors became available.)

Nuclei most often used for Chemical-shift NMR are $^1H$ (protons) and $^{13}C$. Chemical shifts of $^1H$ are not more than 10 ppm of the NMR resonance frequency of isolated protons. To make $^1H$ chemical shift NMR work a relative inhomogeneity of the external magnetic field $B_0$ of far less than 1 ppm is required. Carbon-13 NMR ($^{13}C$ NMR) chemical shifts are typically at least an order of magnitude greater and hence require less stringent magnet homogeneity. But $^{13}C$ has a low natural abundance of only 1% of the total carbon content and a gyromagnetic ratio which is a quarter of that of hydrogen. This results for $^{13}C$ in a NMR sensitivity that is approximately 6000 times lower than the NMR sensitivity of $^1H$ (at the same $B_0$). Carbon-13 spectroscopy is especially useful in determining the chemical composition of carbon-containing compounds and, as said before, requires not such a very homogeneous magnetic field as $^1H$ spectroscopy.

Some uses of carbon-13 spectroscopy are discussed in prior art. U.S. Pat. No. 5,306,640, issued to Vinegar et al., discusses a method for more accurately determining in-situ oil and brine saturation in porous samples using NMR. Vinegar '640 uses NMR methods for rapid non-destructive analysis of sponge core and obtains information about oil composition and viscosity, which can be obtained simultaneously. The method differentiates between crude oil and water based on frequency-resolved chemical shift NMR spectroscopy of the crude oil and water in a porous medium. The patent of Vinegar '640 uses carbon-13 NMR spectroscopy and a weighted carbon density of the oil to determine a volume of oil.

The method of U.S. Pat. No. 6,111,409, issued to Edwards et al., discusses a method of characterizing a fluid sample withdrawn from an earth formation. Edwards '409 discusses performing nuclear magnetic resonance spin echo measurements on the fluid sample at a nuclear magnetic resonant frequency of carbon-13. Amplitudes of the spin-echo measurements are summed. The summed measurements are spectrally analyzed. The fluid is characterized by determining whether aromatic hydrocarbons are present. This characterization is done by measuring an amplitude of the spectrally analyzed spin echo measurements at about 130 parts per million frequency shift from the carbon-13 resonant frequency. The fluid is also characterized by determining whether aliphatic hydrocarbons are present by measuring an amplitude of the spectrally analyzed spin echo measurements at about 30 parts per million frequency shift.

Carbon-13 NMR signals are typically weak due to the low natural abundance of this nucleus and the low polarizations attainable in thermal equilibrium at normal magnetic fields and temperatures downhole. On the other hand, a high-resolution $^{13}C$ chemical shift NMR spectrum can be powerful in analyzing the chemical composition of hydrocarbons downhole. There is a need for a method of enhancing NMR signals in a downhole environment. The present invention fulfills that need.

SUMMARY OF THE INVENTION

One embodiment of the present invention is an apparatus and method for characterizing a fluid sample obtained downhole using an enhanced nuclear magnetic resonance (NMR) Carbon-13 signal. This isotope is found in all hydrocarbons and connate formation fluids and in borehole mud, typical of the downhole environment. The $^{13}C$ NMR signal strength is very much improved by polarization enhancement. The $^{13}C$ nuclei are being hyperpolarized beyond the thermal equilibrium polarization normally possible in the applied static magnetic field. The apparatus of the present invention can be conveyed downhole on a wireline device or on a measurement-while-drilling device. The apparatus comprises a sensor device, a fluid inlet connected to the sensor device for obtaining a fluid from the earth formation into the sensor, and a fluid discharge for discharging the fluid sample from the sensor device into the borehole. In one embodiment an agent chamber, connected to the fluid inlet, injects its contents, typically a polarizing agent, into the fluid inlet.

In a first aspect the polarizing agent is responsive to electron spin resonance, i.e. it contains atoms or molecules with unpaired electrons. The mixture (here called the sample) of formation fluid and polarizing agent is transferred into the NMR/ESR probe that is in the magnet. In the magnet the sample is first magnetized to thermal equilibrium. By subjecting the sample to high frequency (HF), meeting the ESR resonance condition, and making use of the Overhauser effect (OE), the polarization of the $^{13}C$ nuclei can be enhanced beyond equilibrium by a hyperpolarization factor of up to 2600 (theoretical maximum). Once the $^{13}C$ nuclei are hyperpolarized any known $^{13}C$ measurement can be executed by radiating the appropriate RF pulse sequence or by performing a CW NMR measurement at the $^{13}C$ resonance frequency. The amplitude of the received $^{13}C$ signals will be enhanced by the hyperpolarization factor. A description of the Overhauser Effect and also of the Nuclear Overhauser Effect is found in the monograph of C. P. Slichter, "Principles of Magnetic Resonance", 3rd enlarged and updated edition 1990.

In a second aspect the phenomenon of the Nuclear Overhauser Effect (NOE) is used to generate the hyperpolarization of the $^{13}C$ nuclei. The energy difference of the spin up and spin down states in $^1H$ is about 4 times of that of the energy difference of the two spin states in $^{13}C$. Analogous to the OE of the previous chapter the $^1H$ transition can be saturated (instead of the unbound electrons) by radiating RF at the $^1H$ resonance frequency. The $^1H$ spin system can couple to the spin system of $^{13}C$. The result is an increase in the population difference between spin up and spin down states of the $^{13}C$ system beyond the thermal equilibrium, i.e. the carbon nuclei are being hyperpolarized. Once the $^{13}C$ is hyperpolarized the $^{13}C$ NMR is executed with enhanced signal amplitude and enhanced signal-to-noise ratio as described elsewhere in this patent application. The advantage of the described method is that hydrogen is naturally present in any sample of formation fluid. In contrast to OE no extra polarization agent needs to be used.

In a third aspect of the invention the polarizing agent can be polarized by optical pumping with circularly polarized light (most conveniently generated by a LASER) and making use of the Spin Induced Nuclear Overhauser Effect (SPINOE) of which details can be found in Boyd M Goodson, "Advances in Magnetic Resonance, Nuclear Magnetic Resonance of Laser-Polarized Noble Gases in Molecules, Materials, and Organisms", Journal of Magnetic Resonance, vol. 155, 157-216 (2002). The polarizing agent can be polarized in the agent chamber before being injected into the fluid sample. Alternatively it may be possible to polarize the polarizing agent after mixing with the formation fluid sample either still outside the magnet or inside. Different variants of optical pumping and SPINOE are needed depending on these alternatives (see below). Typically the polarizing agent is a noble gas with traces of other gases. In one instance, the polarizing agent can be xenon with traces of a vaporized alkali metal and nitrogen.

Characterizing the fluid sample typically involves obtaining a NMR signal (FID) of the hyperpolarized $^{13}$C. Such NMR signals arise from any substances containing carbon nuclei, in particular from hydrocarbons. The carbon-13 signal is enhanced due to a process of polarization transfer between the nuclei of the polarized polarizing agent and the carbon-13 atoms. A process known as a Spin Induced Nuclear Overhauser Effect (SPINOE) can serve as a mechanism for nuclear spin transfer.

An alternative method of characterizing the fluid sample involves high resolution (or chemical shift) NMR at the resonance frequency of the hyperpolarized agent, e.g. xenon.

The present invention is a method for characterizing a fluid sample withdrawn from an earth formation. Nuclear magnetic resonance measurements are performed on fluid samples obtained downhole at a magnetic resonant frequency of typically carbon-13. These measurements are transformed into a frequency spectrum, e.g. by Fourier transform or any other applicable method. The frequency spectrum is analyzed and the chemical composition of the fluid sample (as far as the molecules contain carbon) is determined.

In a first embodiment the method further comprises measuring a magnitude of a static magnetic field used to make the $^{13}$C NMR measurements and superimposing a selectable magnitude magnetic field on the static magnetic field to compensate for temperature induced changes in the magnitude of the static magnetic field. A magnetic field sensing device, e.g. hall sensor, is used to measure the magnetic flux density. Alternatively and preferably the $^1$H NMR resonance of the fluid under test may be used to measure and regulate the static magnetic field.

In a second embodiment the method further comprises measuring a magnitude of a static magnetic field used to make the $^{13}$C NMR measurements, but no selectable magnetic field is superimposed. After acquisition of the $^{13}$C NMR signals these signals will then become frequency corrected using the result of the magnetic field measurement.

The homogeneity of the static magnetic field may be optimized by superimposing a number of selectable magnetic field gradients. The magnetic field homogeneity may be tested by analyzing the $^1$H NMR signal either in the time domain by testing the length of the $^1$H FID or after transformation into a frequency spectrum by testing the width of the resonance line. A regulation algorithm varies the superimposed fields so that the length of the $^1$H FID is maximized or the resonance line width is minimized or matches a predefined shape. Instead of pulsed $^1$H NMR CW $^1$H NMR may be used for the magnetic field regulation.

The method can further comprise performing nuclear magnetic resonance spin echo amplitude measurements, e.g. using a CPMG sequence, at a resonant frequency of hydrogen nuclei, and determining a relaxation rate or a distribution of relaxation rates of the hydrogen nuclei.

BRIEF DESCRIPTION OF THE DRAWINGS

The present invention is best understood with reference to the accompanying figures in which like numerals refer to like elements, and in which.

DETAILED DESCRIPTION OF THE INVENTION

Figure 1:
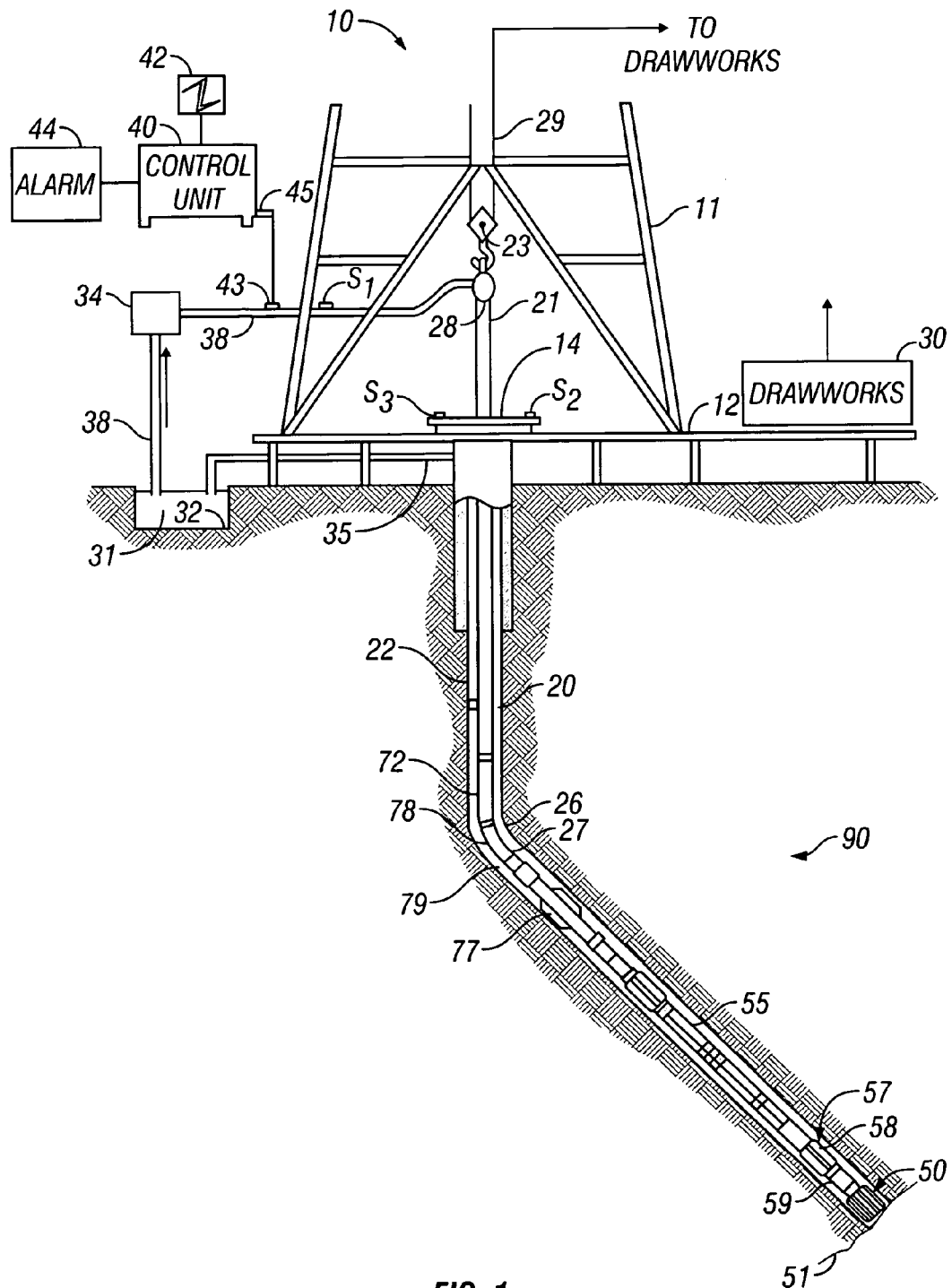
FIG. 1 (Prior Art) shows a measurement-while-drilling device suitable for use with the current invention.

FIG. 1 shows a schematic diagram of a drilling system 10 with a drillstring 20 carrying a drilling assembly 90 (also referred to as the bottom hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 28 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ placed in the line 38 can provide information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the invention, the drill bit 50 is rotated by only rotating the drill pipe 22. In another embodiment of the invention, a downhole motor 55 (mud motor) is disposed in the drilling assembly 90 to rotate the drill bit 50 and the drill pipe 22 is rotated usually to supplement the rotational power, if required, and to effect changes in the drilling direction.

In one embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the invention, a drilling sensor module 59 is placed near the drill bit 50. The drilling sensor module contains sensors, circuitry and processing software and algorithms relating to the dynamic drilling parameters. Such parameters can include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface.

Alternatively, the signals can be processed using a downhole processor at a suitable location (not shown) in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 can include a computer or a microprocessor-based processing system, memory for storing programs or models and data, a recorder for recording data, and other peripherals. The control unit 40 can be adapted to activate alarms 44 when certain unsafe or undesirable operating conditions occur.

Figure 7:
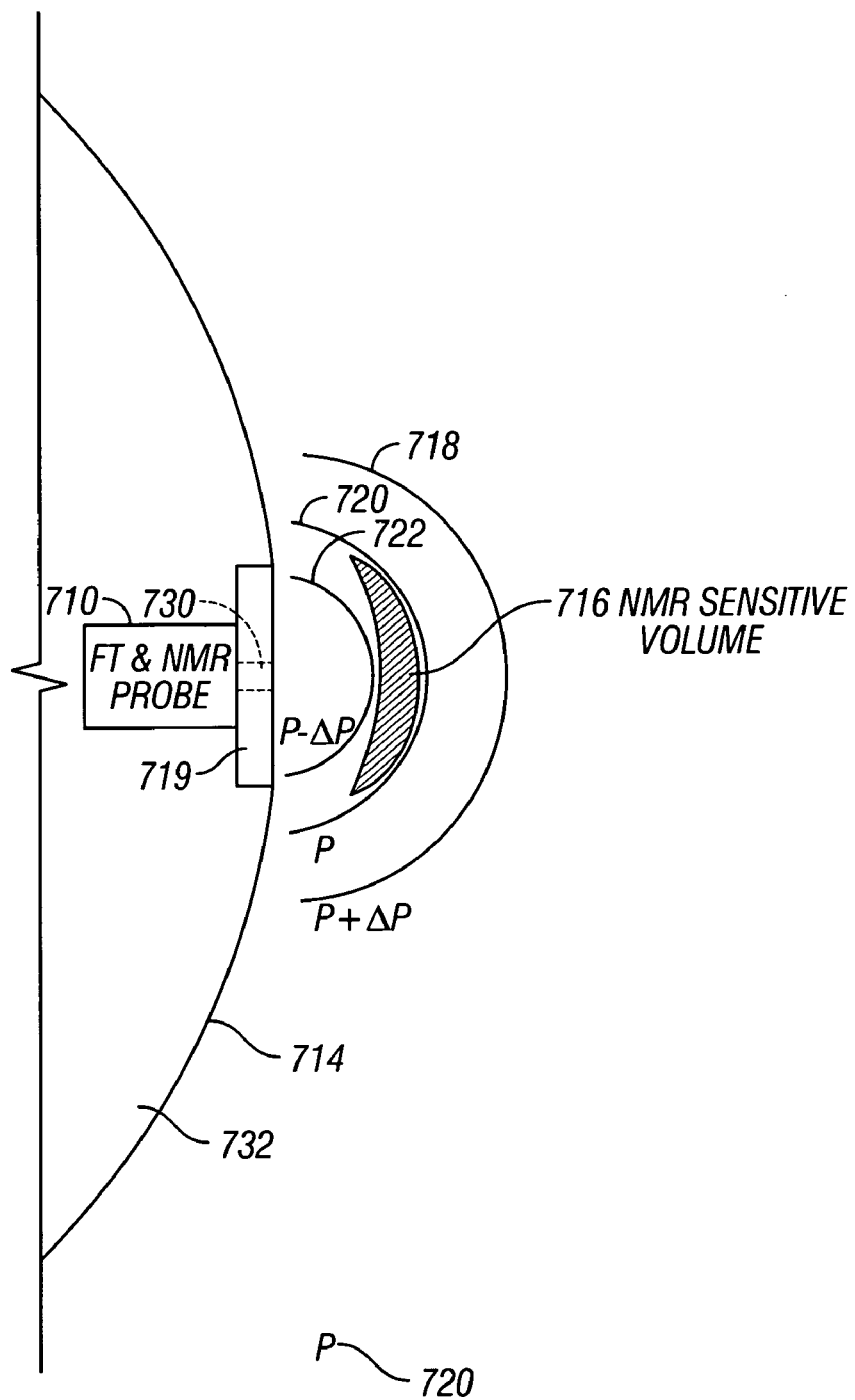

FIG. 7 shows a pad mountable saturation-determining device of U.S. patent application Ser. No. 10/404,408, by Georgi, filed on Apr. 1, 2003, having the same assignee as the present invention, and the contents of which are incorporated herein by reference. Such a saturation-determining device can be, for example, an NMR or resistivity device and a formation testing tool mounted in an extensible probe and pad device on either a logging while drilling tool or a wire line formation tester probe assembly, such as the Baker Atlas Reservoir Characterization Instrument (RCI). RCI is detailed in U.S. Pat. No. 5,303,775 by Michaels et al., which is incorporated by reference in its entirety. A monitoring while drilling formation tester extensible probe assembly is detailed in U.S. patent application Ser. No. 09/910,209, by Krueger et al. cited above. In either configuration, wire line or logging while drilling, the present invention provides for relative permeability determination over time derived from formation and pressure draw down testing over time combined with NMR or resistivity saturation measurements over time to determine relative permeability. As shown in FIG. 7, the resistivity/NMR saturation measurement is confined to an area associated with a localized resistivity/NMR region of interest 716 close to the borehole 732 within a few radii of the formation test tool probe, that is, the radius of the internal passage or orifice provided for ingress of formation fluid 730 and egress of completion fluid through the borehole wall 714 to the formation. The probe 710 extends from the downhole tool to press and seal the probe face 719 against the borehole wall 714. Formation fluid is extracted from the borehole through the probe 710. Completion fluid is injected into the formation through the probe 710. The provision of adjacent formation testing and NMR equipment in the same downhole tool enables concurrent determination of saturation level and absolute permeability with NMR (Coates-Timur equation) data and mobility data from draw down-buildup analysis performed by the formation testing equipment.

The invention of U.S. patent application Ser. No. 10/404,408, by Georgi, also discusses injecting fluids comprised of hyperpolarized elements in the formation. These hyperpolarized elements increase the NMR signal and response, thereby increasing the signal to noise ratio for the NMR measurements. In accordance with the present invention, the method of U.S. patent application Ser. No. 10/404,408, by Georgi, can be performed by drawing the fluid of the borehole into a sensor device conveyed by the drilling tool into the borehole and injecting these hyper-polarized element into the fluid upon entering the sensor.

Typical NMR methods used in a borehole employ a geometry in which the testing device is inserted into the borehole and measures properties of the medium that surrounds it. For downhole testing of solid earth formations, this geometry holds many advantages. Borehole fluid samples can also be drawn into a chamber situated within the drill tool and thereby be surrounded by NMR coils which can deliver RF pulses. One example of this is seen in U.S. Pat. No. 6,111,409, issued to Edwards et al., having the same assignee as the present invention, and the contents of which are incorporated by reference.

Figure 2:
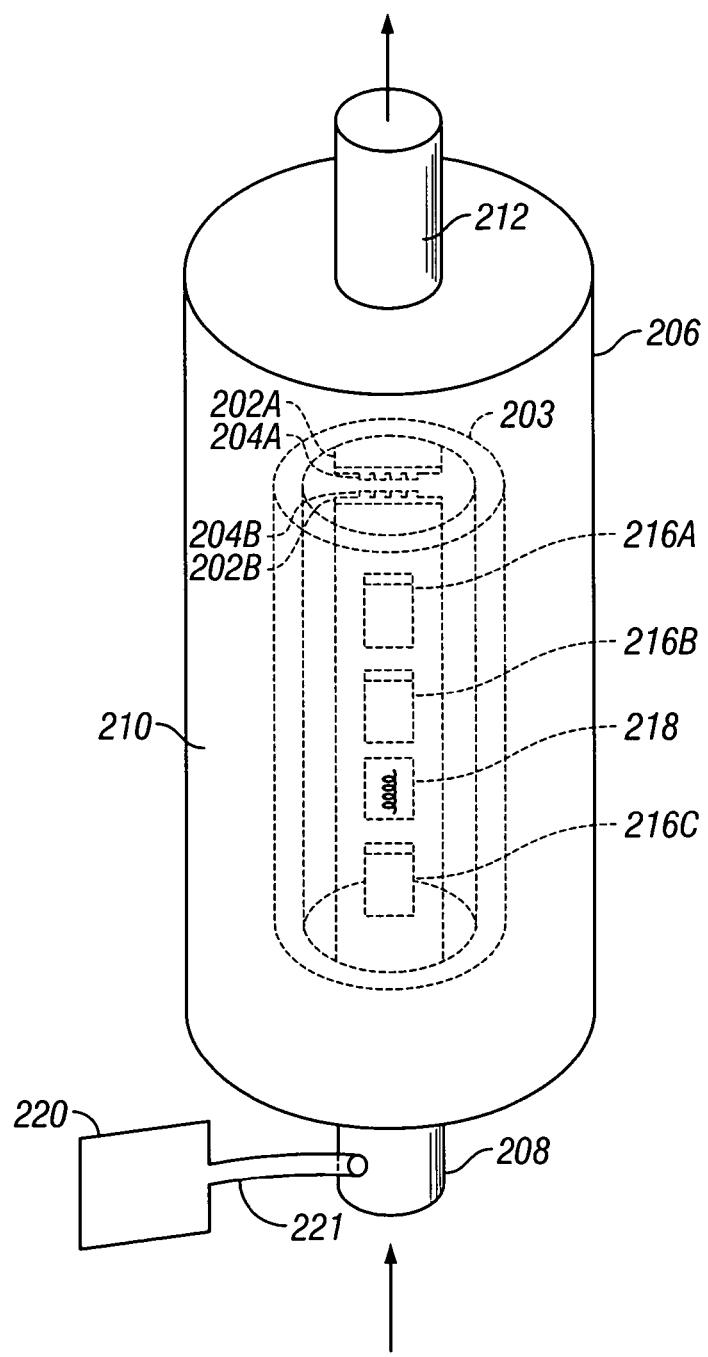
FIG. 2 shows a nuclear magnetic resonance (NMR) sensor according to the invention disposed in a hydraulic isolation chamber, FIG. 3 (Prior Art) shows an end view of the NMR sensor of the invention detailing the location of permanent magnets and antennas, FIG. 4 (Prior Art) shows a functional block diagram of circuits used to make NMR spectroscopy measurements using the NMR sensor of the invention, FIG. 5 (prior art) shows the principle of the Overhauser Effect (OE), FIG. 6a (Prior Art) shows the principle of polarizing an alkali atom by optical pumping with circularly polarized light, FIG. 6b (Prior Art) shows polarization of xenon nuclei via collision and spin exchange, FIG. 7 (Prior Art) shows a pad-mounted tool comprising an NMR or resistivity device and formation testing probe, FIGS. 8A-8C (Prior Art) show representative analyses for connate fluid, aromatic-based mud filtrate, and aliphatic-containing crude oil, using the method of the invention, FIG. 9 (Prior Art) shows a timing diagram for NMR measurement sequences made using the apparatus of the invention, FIG. 10 (Prior Art) shows a diagram of the processes of nuclear spin polarization transfer, FIG. 11 (Prior Art) shows a progression of the spin transfer interactions with the various degrees of polarization at each stage, and FIGS. 12, 12A, 12B (Prior Art) show configurations of magnets, antenna and shield suitable for use in obtaining in situ measurements with the present invention.

FIG. 2 shows a nuclear magnetic resonance ("NMR") sensor 210 suitable for use with the present invention which can be disposed at any convenient location along an hydraulic line. As fluid is withdrawn from the earth formation, it enters the sensor 210 through a fluid inlet 208 in a pressure-sealed chamber 206. The pressure-sealed chamber 206 can be disposed in a convenient location in the instrument housing to hydraulically isolate the fluid withdrawn from the earth formation. After NMR measurements are performed on the fluid in the chamber 206, continued operation of the pump (not shown) can cause the fluid to be moved through a fluid discharge 212 in the chamber 206 into the pump for eventual disposal either into the wellbore or into a sample tank (not shown). It should be noted that the sensor 210 can also be located in the pump discharge line if it is convenient for the system designer.

Agent chamber 220 is connected via flow channel 221 to fluid inlet 208. The contents of agent chamber 220 can be injected into the fluid in fluid inlet 208 prior to the entrance of the fluid into pressure-sealed chamber 206. Typically, agent chamber 220 contains a polarizing agent for use in enhancing the NMR signal of the fluid sample using a method of the present invention.

The sensor 210 can include permanent magnets 202A, 202B made from AlNiCo or Samarium-Cobalt or similar magnetic material having remanence magnetization which is relatively stable with respect to temperature. In this embodiment of the invention, the magnets 202A, 202B can be surrounded by a substantially cylindrical flux closure or "yoke" 203. Each magnet 202A, 202B can have its own pole piece 204A, 204B on the respective face of each magnet directed towards the center of the sensor 210. The magnets 202A, 202B, yoke 203, and pole pieces 204A, 204B provide a substantially homogeneous static magnetic field in the center of the sensor 210. The direction of magnetization of the magnets 202A, 202B is substantially perpendicular to the longitudinal axis of the sensor 210. Three radio frequency antennas 216A, 216B, 216C are disposed along the axis of the sensor 210 in between the magnets 202A, 202B. The antennas 216A, 216B, 216C are used for sequential NMR experiments on the fluid in the center of the sensor 210. The sensor 210 can include a Hall probe 218 or similar device for measuring the magnitude of the static magnetic field induced by the magnets 202A, 202B so that the magnitude and the homogeneity of the field can be adjusted for changes in the strength of the 202A, 202B magnets with temperature, as will be further explained.

Figure 3:
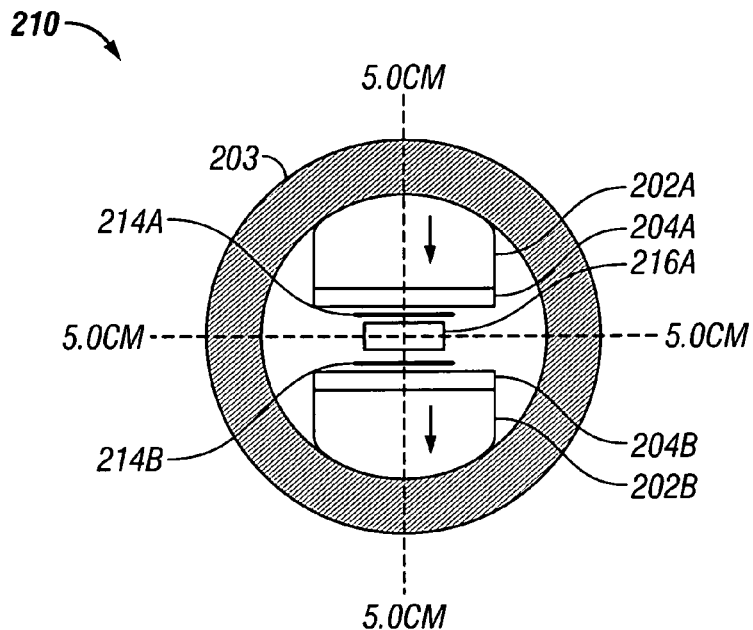

The structure of the sensor 210 can be better understood by referring to an end view in FIG. 3. The magnets 202A, 202B are each polarized as shown by an arrow thereon, generally perpendicular to the longitudinal axis of the sensor 210. The axial length of the sensor 210 should be much longer than the diameter of the region in the center of the sensor 210 having substantially homogenous static magnetic field, so that NMR experiments can be performed in different locations along the length of the sensor by each of the three antennas (216A, 216B, 216C in FIG. 3). Pole pieces 204A, 204B can be made of a high magnetic permeability material such as soft iron or the like and can be attached to inner face of each magnet 202A, 202B. The cylindrical yoke 203 can contact each magnet 202A, 202B on the face opposite the location of the pole pieces 204A, 204B. The yoke 203 can be made from a high magnetic permeability material similar to that used for the pole pieces 204A, 204B. The combination of yoke 203, pole pieces 204A, 204B and the magnets 202A, 202B provides a substantially homogeneous static magnetic field between the magnets 202A, 202B, the field polarized in the same direction as the polarization direction of the magnets 202A, 202B. Shim coils 214A, 214B can be located in between the magnets 202A, 202B. The shim coils can be connected to controllable direct current (DC) power sources to provide supplemental static magnetic fields for compensating changes in the magnetic field strength and homogeneity resulting from changes in ambient temperature. An ensemble of shim coils and controllable DC power supplies may be used to remove lower and higher order static field gradients in all three dimensions to optimize field homogeneity. The location of the RF antennas with respect to the magnets 202A, 202B and shim coils 214A, 214B is shown generally at the uppermost antenna 216A. The antennas (216A, 216B, 216C in FIG. 3) can be wire coils wound so that the RF magnetic field induced by the antennas is substantially parallel to the longitudinal axis of the sensor 210. This direction is also perpendicular to the direction of the static magnetic field and is therefore suitable for performing NMR experiments. The arrangement shown in FIGS. 2 and 3 is only an example of arrangements of permanent magnet and antennas which have the requisite properties for conducting NMR experiments in a fluid sample. Other arrangements of permanent magnet and antenna are possible, so the arrangement shown in FIGS. 2 and 3 is not to be construed as a limitation on the invention. The principle requirements for magnets and antennas is that the magnet induce a substantially homogeneous magnetic field in the location of the fluid to be analyzed, and that the antenna induces an RF magnetic field which is also substantially homogeneous and perpendicular to the static magnetic field in the location of the fluid to be analyzed.

The arrangement of magnets, yokes and antennas shown in FIGS. 2 and 3 provides a substantially homogeneous static magnetic field in a cylindrical volume in the center of the sensor 210. If the cylindrical yoke 203 has an external diameter of about 6 cm as shown in FIG. 3, the homogeneous static magnetic field will exist within a cylindrical volume of about 1 cm. in diameter.

Figure 4:
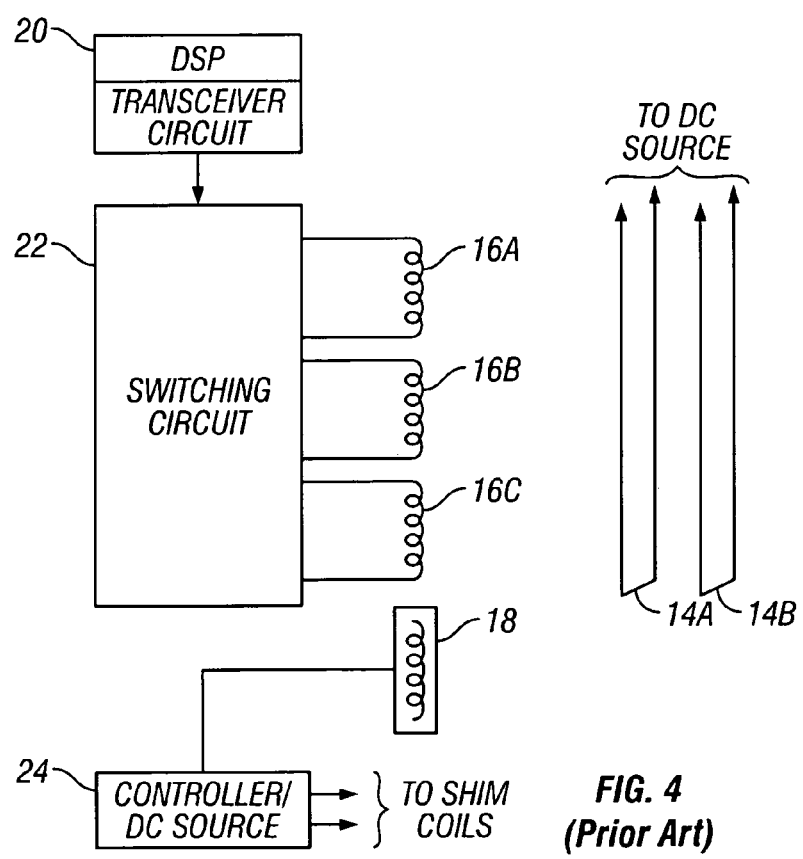

Operation of the sensor 210 can be better understood by referring to FIG. 4. The antennas 216A, 216B, 216C can be connected to a transceiver circuit 420 through a switching circuit 422. The transceiver circuit 420 generally can include a radio frequency power source which generates controlled-duration pulses or RF power, and switching circuits for selectively connecting the selected antenna (216A, 216B or 216C) between the RF source and a receiver circuit (not shown separately). The receiver circuit is for detecting voltages induced in the selected antenna by nuclear magnetic resonance. Circuits suitable for the transceiver 420 are described, for example, in U.S. Pat. No. 5,712,566 issued to Taicher et al. The transceiver 420 also can include digital signal processing ("DSP") circuits for performing certain calculations on the measurements.

Irrespective of the magnetic material from which they are made, the magnets (202A, 202B in FIG. 3) will to some degree have remanence magnetization which is affected by the ambient temperature around the magnets. It is not at all unusual for well logging instruments to be subjected to a temperature range from 0° to 200° C. Since the NMR experiments performed by the sensor (210 in FIG. 3) are intended to be made in a homogeneous static magnetic field, the sensor 210 includes so-called "shim" coils 214A, 214B which selectively induce a magnetic field superimposed on the static magnetic field induced by the magnets (202A, 202B in FIG. 3). The intensity of the total static field can be measured by the Hall probe 218 or similar device, which can be connected to a control circuit 424. The control circuit 424 applies a direct current the shim coils 214A, 214B, the magnitude of which is related to the output of the Hall probe 218, so that the total magnitude of the static magnetic field in between the magnets 202A, 202B can be maintained substantially constant. As is understood by those skilled in the art, the magnetic resonant frequency of selectively RF-excited nuclei will depend on the magnitude of the static magnetic field in which they are polarized. By maintaining a substantially constant static magnetic field magnitude, the need to adjust the frequency of the RF magnetic field for NMR experimentation can be reduced or eliminated. The shim coils 214A, 214B and source 424 should be able to provide about 100 Gauss superimposed field magnitude to be able compensate the static magnetic field for changes in remanence magnetization of the magnets (202A, 202B in FIG. 3). The amount of static field amplitude required to be provided by the shim coils 214A, 214B will depend on the type of magnet material used for the magnets. Thermally more stable magnet materials such as AlNiCo or Samarium Cobalt will require smaller field adjustment using the shim coils 214A, 214B than other magnet materials such as ferrite. The resonance of a $^1$H NMR measurement of the sample under test may be used instead of a Hall probe to measure the magnitude of the static magnetic field and its homogeneity. An ensemble of shim coils and controllable DC power supplies may be used to remove lower and higher order static field gradients in all three dimensions to optimize field homogeneity and to adjust the field strength for the chosen nominal magnitude. Alternatively, instead of adjusting the magnitude of the static field, the $^{13}$C NMR reference frequency can be adjusted instead.

Figure 9:
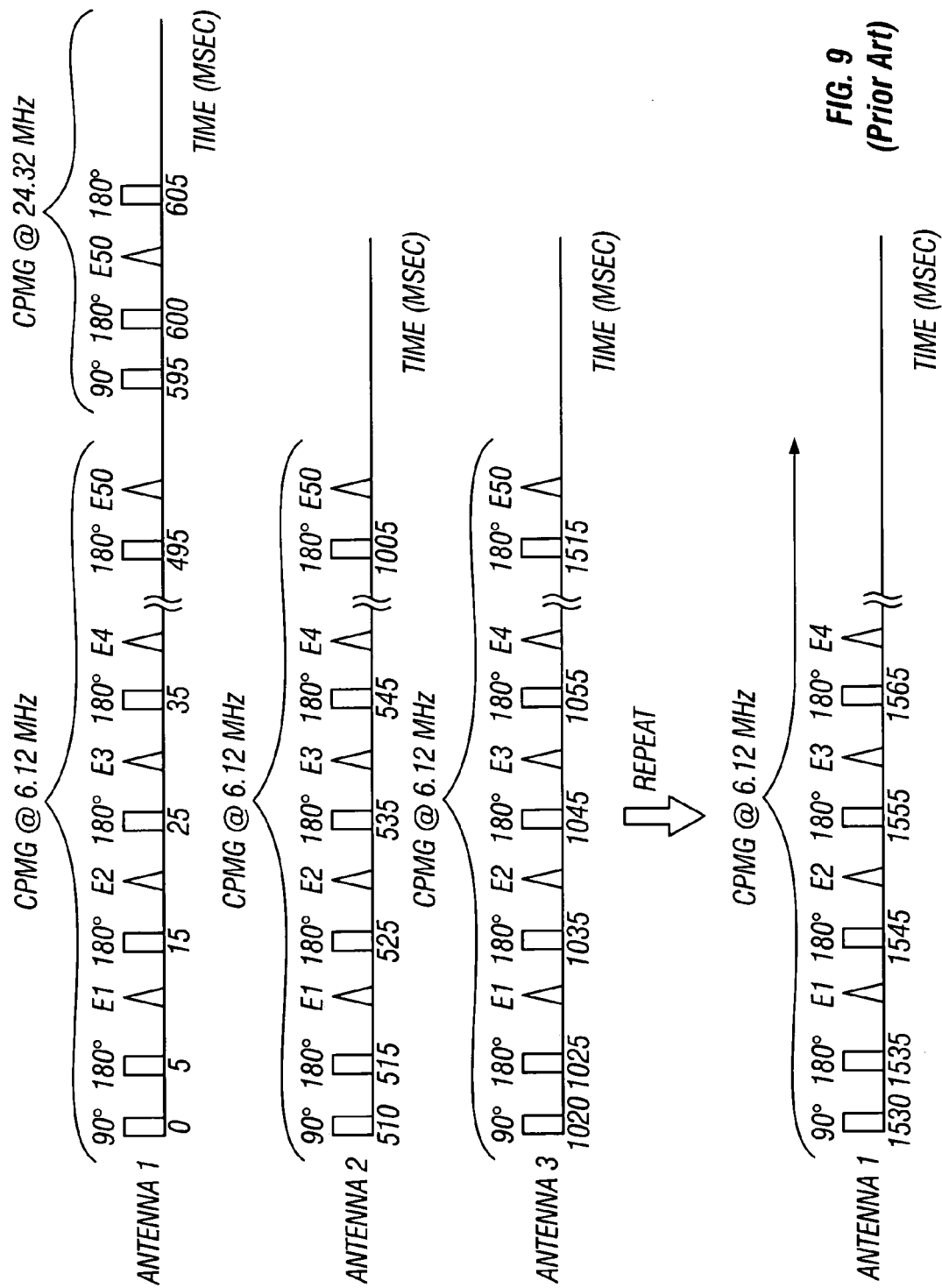

Without hyperpolarization of the carbon-13 nuclei the $^{13}$C signal has a very low amplitude for this reason a measurement sequence according to FIG. 9 is needed, preferably these spin echo sequences are executed twice at 30 ppm and 130 ppm from the nominal $^{13}$C resonance frequency to get optimal conditions for these resonances of carbon nuclei in aromatic and aliphatic hydrocarbons (ref. U.S. patent Carl Edwards??). Many echoes may be accumulated on top of each other to increase the signal-to-noise ratio.

With the employment of one or the other method of polarization enhancement according to this invention the carbon signal amplitude may be so high that the sequences of FIG. 9 are not needed but a single FID is acquired after one RF pulse. This very simple pulse "sequence" may be repeated several times and the FIDs accumulated. The resulting accumulated FID is then transformed by Fourier transform or another method into a frequency spectrum. A person trained in the art of chemical analysis by $^{13}$C NMR can without or with the help of a computer program interpret this spectrum and determine the chemical composition of hydrocarbons in the formation fluid sample.

Figure 5:
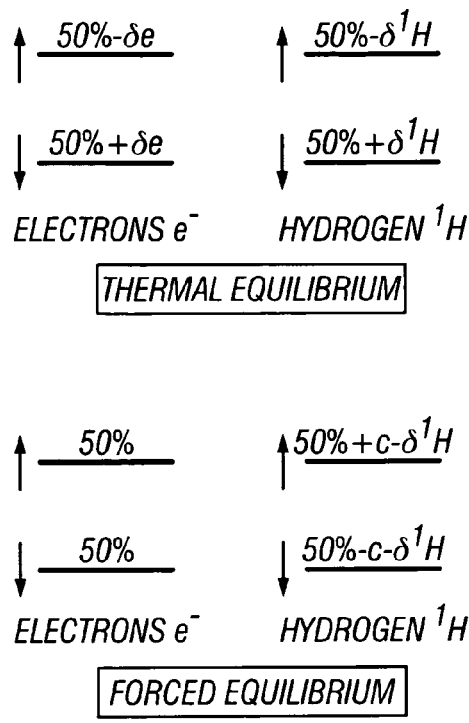

Overhauser predicted (see A. W. Overhauser, Phys. Rev 91, 476 (1953) and A. W. Overhauser, Phys. Rev. 92, 411 (1953)) that if one saturated the conduction electron spin resonance in a metal, the nuclear spins would be polarized 1000-fold more strongly than their normal polarization in the absence of the saturation. This is known as the Overhauser Effect (OE). The experiment was subsequently successfully performed by Carver and Slichter (see Carver et al. Phys. Rev. 92, 211 (1953) and Carver et al. Phys. Rev. 102, 975 (1956). Carver went on to show that this form of polarization was not restricted to a metal. In fact, it is not necessary to transfer polarization between electrons and nuclei. One can transfer polarization from nucleus to nucleus. This is known as the Nuclear Overhauser Effect (NOE). Both effects are used as part of this invention. In one aspect of the invention the hyperpolarization of carbon-13 is achieved by the Overhauser effect (OE) of which the principle is shown in FIG. 5. The upper part of FIG. 5 shows the system in thermal equilibrium in a magnetic field. The higher energy states of electrons and $^1$H nuclei are less populated. This follows from the fact that the population of energy levels follow a Boltzmann distribution. A similar result occurs for $^{13}$C nuclei (not shown in FIG. 5). The factor δe in the population of the electrons in spin down and spin up state is approx. $10^{-3}$ while the equivalent factor $\delta^{13}$C is less than $10^{-6}$ at a magnetic flux density of 1 T and 20° C. Now referring to the lower part of FIG. 5, by radiating an RF field onto the electron spin resonance the populations of both electron energy levels have become equalized. By coupling of the electrons with the nuclei this increases the population of the upper energy level of the nuclei very much and depopulates the lower level accordingly. The $^1$H or $^{13}$C nuclei posses now a high population difference, which is synonymous to a high polarization in excess of the thermal equilibrium. In this embodiment of the invention, the ESR-active agent is stored in a tank in the tool. A small amount is added to the fluid sample extracted from the formation. The sample is irradiated at the ESR resonance frequency to enhance the polarization of the nuclei under test and straight after that (less than the NMR T1) the NMR measurement (typically $C^{13}$) is executed This method has been used for medical applications, where it is necessary that the ESR-active agent be non-toxic. For NMR applications in a wellbore, the stringent restriction of non-toxicity can be relaxed.

In a second aspect of this invention the hyperpolarization of $^{13}$C is achieved by the Nuclear Overhauser Effect (NOE) between $^1$H and $^{13}$C. This is similar to the Overhauser Effect, but in this method the spin exchange is not between electrons and nuclei but between two kinds of nuclei of which the one with the wider energy splitting (higher gyromagnetic ratio, here 1H) is being saturated. Under Certain conditions, depending on the relaxation times and concentrations of the kind of nuclei involved, the population difference of the nuclei with the lower gyromagnetic ratio (here $^{13}$C) is increased and hence becomes hyperpolarized. Since hydrogen nuclei are already present in the formation fluid, it is not necessary to add any particular agent for making measurements based on NOE for evaluation of a $^{13}$C signal. All that is necessary is to apply a (pulsed) RF field at the resonance frequency of $^1$H.

Figure 6A:
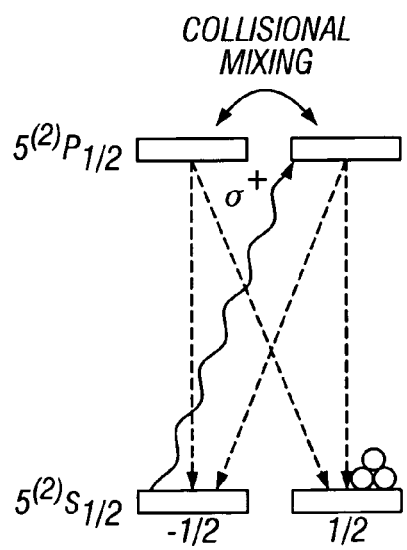

In a third aspect of the invention optical pumping is used to achieve hyperpolarization. One such mechanism is shown in FIG. 6a. This figure shows the S and P electron spin states of an alkali atom. No magnetic field is present which is why the two S spin states have equal energy and also the two P spin states. The dotted-line pointers indicate spontaneous emission. In thermal equilibrium both S states are equally populated and the two P states are virtually not populated at normal temperatures. Radiating with light with a wavelength appropriate to the energy difference between S and P state would populate both P states to some degree. But still there would be no population difference between the two S states. The situation is different if we use circularly polarized light. This is also indicated in FIG. 6a. Circularly polarized light has the ability to cause transitions between the two states connected only by the waved line in FIG. 6a. Electrons are continuously pumped from the $S_{-1/2}$ to the $P_{1/2}$ state. From there after a short time they fall back to the S states or while in the $P_{1/2}$ state they may go first into $P_{-1/2}$ state and then fall back to the S states. Once in the $S_{1/2}$ state they are virtually trapped, while the $S_{-1/2}$ state is continuously depopulated by the circularly polarized light. With this mechanism population is accumulated in the $S_{1/2}$ state as indicated by the three little balls in FIG. 6a In the foregoing no magnetic field was present and the exchange between $P_{1/2}$ and $P_{-1/2}$ electron states, for example, was accomplished by collision. If a magnetic field was present the two states would not have equal energy and it could be necessary to radiate the transition frequency into the sample to facilitate the spin coupling.

Figure 6B:
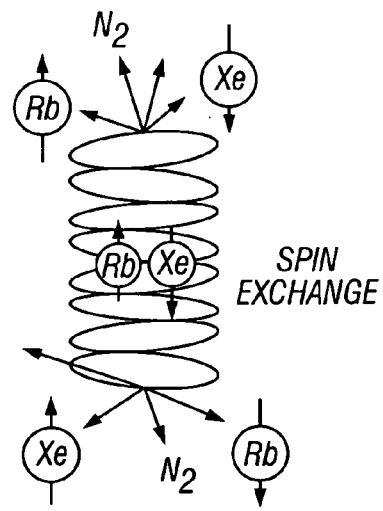

FIG. 6b shows how the electron polarization of an alkali metal such as Rb is transferred to xenon nuclei via collision and spin exchange. A noble gas like xenon is typically used to store the nuclear hyperpolarization because of its long T1 relaxation time. In this embodiment the hyperpolarized xenon is used as the polarizing agent for the $^{13}C$ nuclei.

The polarizing agent such as xenon, for example, can be introduced in small amounts into a fluid of which NMR characteristics are to be measured. The spin polarization of the polarizing agent can be made very high by optical pumping of which details can be found in Goodson (see above). This spin polarization can then be transferred to a spin of a nucleus of an adjacent molecule of the fluid. This spin transfer is known under the name "Spin Polarization Induced Nuclear Overhouser Effect (SPINOE). For example, a spin transfer can occur between a nucleus of xenon and a $^{13}C$ atomic nucleus contained in sampled hydrocarbons. One advantage of the present invention is that such transfer thereby increases the polarization of the nuclei of the fluid molecules far in excess of the thermal equilibrium and hence increases the NMR signal amplitude. The increase in NMR signal amplitude under such a technique can be a factor of the order of 100. Such an amplification of the signal amplitude enables a substantial reduction of the necessary NMR measurement time, theoretically by a factor of 10,000.

The nucleus of a polarizing agent such as a noble gas, e.g. xenon, can be hyperpolarized and this polarization may be transferred from the hyperpolarized gas to a sample. Polarization transfer may occur using a variety of mechanisms. The transient enhancement of a signal as a consequence of cross-relaxation and polarization transfer between the dissolved hyperpolarized gas and the surrounding solution spins is a novel manifestation of the nuclear Overhauser effect (NOE), and is known as the Spin Polarization Induced Nuclear Overhauser Effect (SPINOE). A discussion of SPINOE can be found, for example, in Goodson, "Advances in Magnetic Resonance, Nuclear Magnetic Resonance of laser-Polarized Noble Gases in Molecules, Materials, and Organisms", Journal of Magnetic Resonance, vol. 155, 157-216 (2002). In another mechanism, Cross Polarization (CP) locks both nuclei (noble gas and the target of polarization transfer) with simultaneous electromagnetic fields at two separate frequencies. This creates a quantum transition that enables polarization to be efficiently transferred from one nucleus to another nucleus.

Figure 10A:
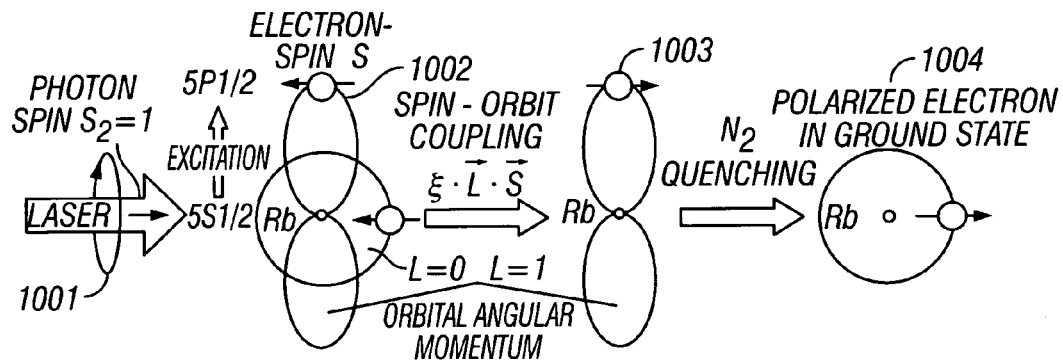
Figure 10B:
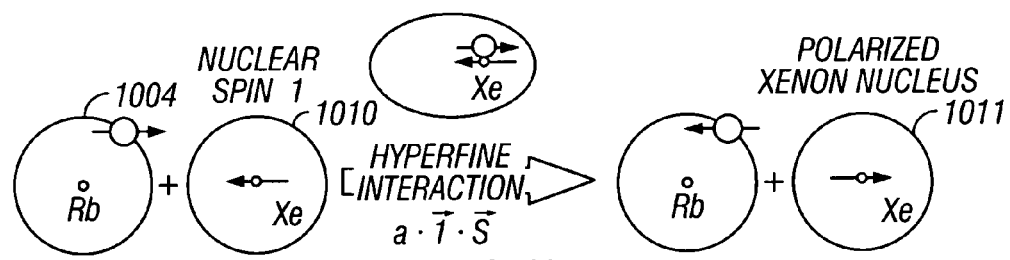
Figure 10C:
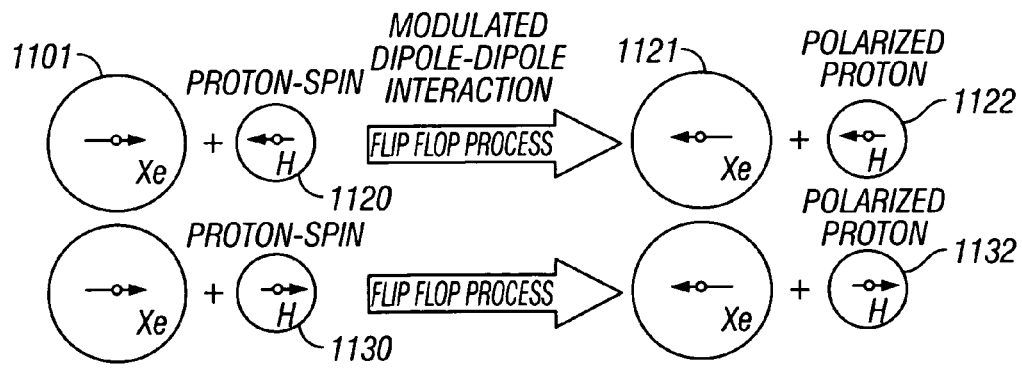

A diagram of the process of transferring spin polarization to the sample fluids is shown in FIG. 10. An intermediate atom can be excited using a variety of methods. As shown in FIG. 10, for instance, a circularly polarized laser beam 1001 can be shined onto an intermediate atom 1002, such as Rubidium, resulting in a excitation of an electron of the intermediate atom by bringing it from the S to the P state. Through a process of spin-orbit coupling, the excitation of the angular moment gives rise to a spin polarization 1003. A quenching process, using $N_2$, for example, leads to a spin-polarized electron in a ground state 1004. Upon contact with a polarizing agent (i.e. xenon), a spin exchange process between the intermediate atom 1004 having a spin-polarized electron and the polarizing agent 1010 enables the transfer of spin polarization from the electron of the intermediate atom (Rb) to the nucleus of the polarizing agent (Xe). Xenon typically has a long $T_1$ time (see Goodson), which is optimal for a polarizing agent. Such a transfer utilizes a hyperfine interaction, and results in a polarized nuclear spin of the polarizing agent 1011. A modulated dipole-dipole interaction can affect the nuclear spin of a hydrogen atom 1120 with which the polarizing agent 1011 comes in contact. As the spin of the nucleus of the Xe atom changes polarization, the spin of the hydrogen nucleus changes its polarization. As shown in FIG. 10, an anti-parallel alignment (a) between the polarizing agent 1011 and hydrogen nuclear spin 1120 leads to another anti-parallel alignment, with the polarities of the polarizing agent and the proton spin reversed (1121 and 1122, respectively). Similarly a parallel alignment (b) between the polarizing agent 1011 and proton spin 1130 leads to a parallel alignment with proton spin reversed 1132. Instead of protons, $^{13}C$ nuclei can be polarized in the same way, or the proton polarization may be transferred to $^{13}C$ nuclei in a further step of SPINOE.

Figure 11:
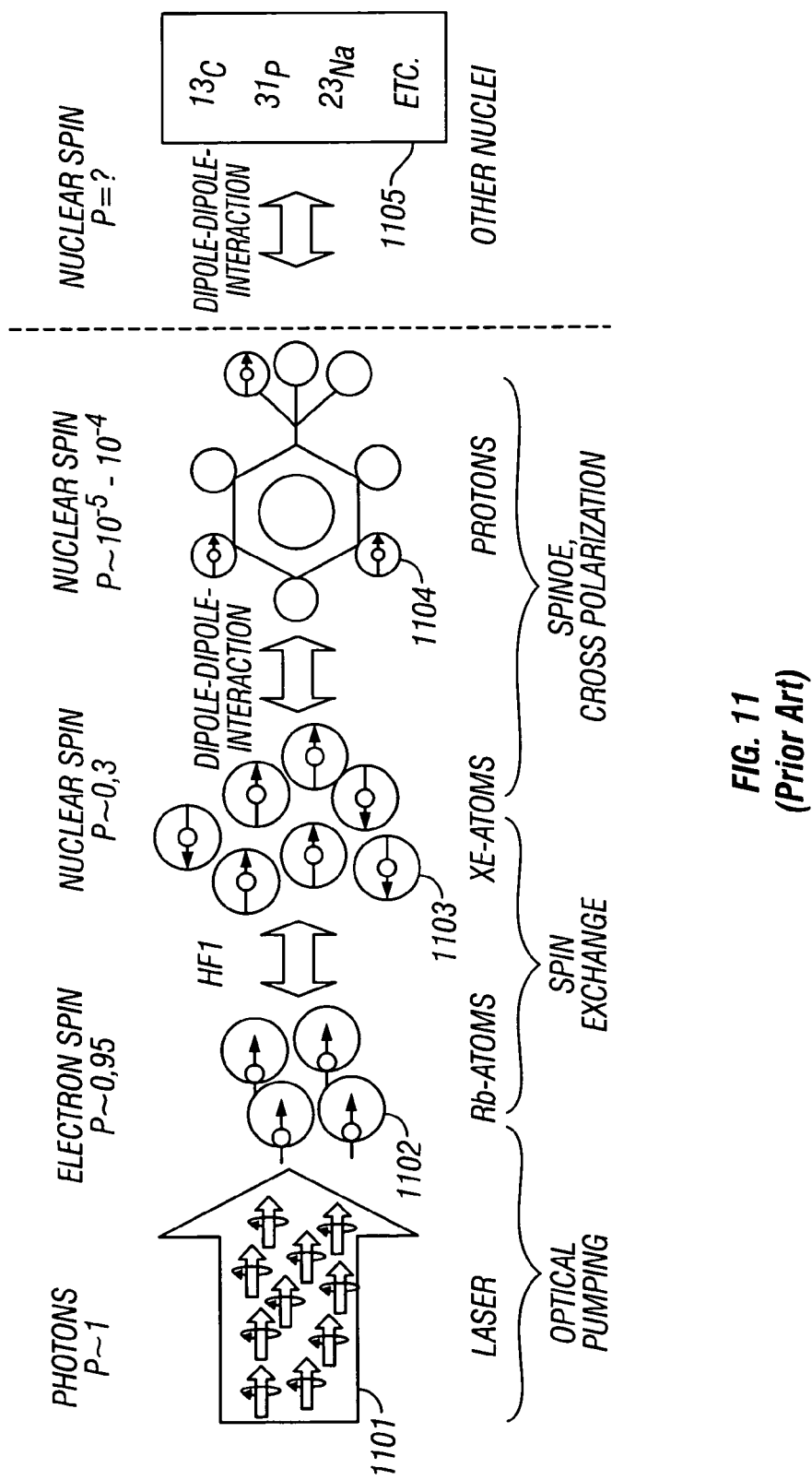

FIG. 11 shows a progression of the spin transfer interactions with the various degrees of polarization at each stage. In the instance where a circularly polarized laser beam 1101 is introduced into the system for excitation purposes, the beam has a nearly total polarization. Upon transfer of the polarization to the intermediate stage atoms 1102, polarization can be found at ~0.95 of the population. After the hyperfine interaction in which spin is transferred from an electron of the intermediate stage atom to the nucleus of the polarizing agent 1103, polarization is at 0.3 of the population. Finally, upon transfer of spin through the dipole-dipole interaction from the nucleus of the polarizing to the nucleus of nearby protons, due to the strength of the interaction, polarization is at $10^{--5}$-$10^{-4}$ of the population of protons 1104. Further dipole-dipole interactions can be used to transfer spin to other atomic nuclei 1105.

In one mode of the present invention, hyperpolarized xenon can be used as the nucleus for chemical shift NMR. The chemical shift range of xenon in different chemical environments is over 7000 ppm wide. While the large shift range results largely from strong electron deshielding in the xenon compounds, a range of over 200 ppm may be obtained merely by dissolving xenon in various liquids. Xenon is generally chemically inert. However, in 1962 Neil Bartlett at the University of British Columbia treated xenon gas with $PtF_6$ and prepared the first noble gas compound consisting of platinum, fluorine and xenon. More than 80 xenon compounds have been made with xenon chemically bonded to fluorine and oxygen. For the purposes of the present invention, the highly polarizable electron cloud of xenon causes it to be relatively lipophilic, permitting xenon to participate in specific interactions with various substances. This makes it possible to characterize recovered formation fluids by performing chemical shift analysis of the NMR spectra of xenon dissolved in said formation fluids. This chemical shift NMR is discussed below with respect to $^{13}$C, but the method may also be used with xenon NMR. In addition, xenon readily adsorbs to numerous surfaces under experimentally convenient conditions. This, together with its lipophilic behavior enables a direct determination of oil saturation in situ. Due to the very high hyperpolarization possible in xenon only a trace amount would be needed for this measurement.

In one mode of the invention, the polarizing agent can be first optically pumped using a laser and later introduced into a chamber containing a fluid sample to be examined using NMR techniques. The spin polarization of the polarizing agent is transferred to the fluid, at which time NMR characterization can be performed.

The unpolarized agent is stored under pressure in a storage tank. After being polarized, the agent is stored again in another pressurized tank before being brought in contact with the fluid sample to be tested by NMR. The length of time the polarized agent can be stored depends on its $T_1$ relaxation time, which for xenon is of the order of half an hour, depending on its purity and the storage vessel material.

As the $T_1$ of the polarizing agent can currently be increased using procedures discussed, for example, in Goodson, then it may be possible to polarize the polarizing agent at the surface and transfer it to the storage tank in the drilling tool before the NMR tool is lowered into the borehole, thereby avoiding the need of optically pumping downhole. In wireline or coiled tubing drilling tools it may be possible to feed polarized xenon continuously down a tube in the wireline or coiled tubing from the surface to the measurement tool downhole.

Alternatively, the polarizing agent can first be introduced into a chamber containing a fluid sample to be examined using NMR techniques. A laser beam tuned to a polarizing frequency of the polarizing agent can then be directed into the chamber. The polarizing agent becomes polarized and then transfers its spin polarization to the nuclei of the fluids to be characterized, for instance, using the spin transfer of SPINOE.

Chemical analysis of hydrocarbons in the formation can be performed at the same time as other tests, i.e. formation pressure testing, without taking formation liquid samples to the surface.

The presence or absence of certain frequency components can be used to determine whether aromatic hydrocarbon compounds and/or aliphatic hydrocarbon compounds are present in the fluid sample. The resolution of spin echo amplitude measurements in the method of the invention is sufficient to calculate relative amplitudes of signal components at 30 and 130 parts per million (ppm) from the base frequency (the frequency of the RF power used to perform the spin echo measurement sequences. Alternatively the complete $^{13}$C spectrum may be obtained, e.g. by sampling FIDs and Fourier transform, or by performing CW NMR, as far as the homogeneity and stability of the static magnetic field is enabling.

To process the digitized spin echoes into characterizing information about the fluid sample, each spin echo in each CPMG sequence can have time correspondent ones of the digitized amplitude measurements summed or averaged over each entire CPMG sequence. The result of the summing is a set of digital amplitude values for each CPMG sequence. In this embodiment of the invention, three antennas 216A, 216B, 216C are provided at different locations along the longitudinal axis of the sensor 210. By including a plurality of antennas each energizing a different volume within the fluid sample, it is possible to acquire NMR signals having improved signal-to-noise in a relatively short time period. The improved signal-to-noise is obtained by summing or "stacking" the spin echoes measured using each antenna 216A, 216B, 216C. The stacking can be performed in a signal processor. The antennas 216A, 216B, 216C can each be selectively energized for performing a CPMG measurement sequence by using the switching circuit 422. As is known in the art, nuclei which have been transversely polarized by NMR spin echo experimentation gradually "relax" or return to magnetic spin orientation aligned with the static magnetic field. During the longitudinal relaxation, no further experimentation on the particular sample is practical. The nuclei of the fluid samples in the location of the non-energized antennas, however, remain substantially polarized along the static magnetic field and can be subjected to NMR spin-echo experimentation during the longitudinal relaxation period (the "wait time") of the previously transversely polarized (the "experimented on") fluid sample. Spin echo amplitudes measured by each of the antennas 216A, 216B, 216C can also be summed to get spin echo amplitude values having improved signal-to-noise. Using three switched antennas is not a limitation on the invention, but is merely illustrative of the principle of multiple measurements made in different portions of the sample to conserve time. It is contemplated that five or more switched antennas can be used with the sensor 210 of the invention. It is further contemplated that two or more of the antennas can be used to conduct CPMG measurements sequences simultaneously where enough such antennas are used in the particular sensor to enable sufficient wait time between measurement sequences at any single antenna. For example, a measurement cycle for a six antenna system could include measuring CPMG sequences at the first and fourth antennas, next at the second and fifth antennas, and finally at the third and sixth antennas. The cycle can then be repeated at the first and third antennas, and so on for an appropriate number of cycle repetitions to obtain a sufficient signal-to-noise ratio.

A timing diagram showing typical CPMG pulse sequences applied to each of the antennas (216A, 216b, 216C in FIG. 4) is shown in FIG. 9. 90° and 180° pulses at the 6.12 MHz resonant frequency can be applied to the first antenna as shown in the upper timing scale in FIG. 9. Each spin echo occurring after one of the 180° pulses is indicated by E1, E2, E3, and on through E50. Immediately after the end of the CPMG sequence at 6.12 MHz at the first antenna (216A in FIG. 4) a CPMG sequence can be applied to the second antenna (216B in FIG. 4) as shown in the second timing scale in FIG. 4, starting at about 510 milliseconds from the initiation of the sensor operation. As the CPMG sequence is completed at the second antenna, a CPMG sequence can be immediately started at the third antenna (216C in FIG. 4). This entire sequence of CPMG sets at successive antennas can be repeated as shown in the bottom timing scale in FIG. 4, representing a CPMG sequence at 6.12 MHz at the first antenna starting at about 1530 milliseconds from the start of the first such CPMG sequence at the first antenna.

After summing, or "stacking", the spin echo amplitude values from all the CPMG measurement sequences, the resulting stacked spin echo amplitude sample values can then be analyzed using a fast Fourier transform or similar spectral analysis, to generate a Fourier spectrum. The Fourier spectrum will include relative amplitude contributions of different frequency components present in the stacked spin echo amplitude values. The presence or absence of certain frequency components can be used to determine whether aromatic hydrocarbon compounds and/or aliphatic hydrocarbon compounds are present in the fluid sample. The resolution of the spin echo amplitude measurements in the method of the invention is sufficient to calculate relative amplitudes of signal components at 30 and 130 parts per million (ppm) from the base frequency (the frequency of the RF power used to perform the spin echo measurement sequences.

For example, carbon-13 in xylene generates characteristic spectral peaks in the range of about 130 ppm from the base frequency of 6.12 MHz. Carbon-13 in typical aliphatic (alkane) compounds including $CH_2$ and $CH_3$ molecular groupings therein has characteristic peaks in the 30 ppm range from the base frequency. See, for example, W. Simons, *The Sadtler Guide to Carbon*-13 *Spectra,* Sadtler Research Laboratories, 1984. As is known in the art, drilling fluids which include hydrocarbon as the liquid phase typically include aromatic compounds. Crude oils typically include some aliphatic compounds. After performing the Fourier transform on the stacked samples, the amplitude of the spectrum at 130 ppm can be measured, and the amplitude of the spectrum at 30 ppm can be measured. Absence of any substantial spectral amplitude at 130 or 30 ppm indicates that the fluid sample does not include any substantial amount of hydrocarbons, either aromatic or aliphatic type. If the amplitude of the 130 ppm portion of the spectrum shows substantial presence of aromatic hydrocarbons, and the drilling fluid contains such aromatics in the liquid phase, it may be inferred that the fluid sample includes a substantial fraction of mud filtrate. Presence of substantial amounts of aliphatic hydrocarbons, as indicated by substantial amplitude of the 30 ppm portion of the spectrum, indicates that the fluid sample in the sensor 10 includes some connate hydrocarbons. It is therefore possible using the spectroscopy technique of the invention, to discriminate between crude oil, and oil based mud filtrate by determining the relative presence of aliphatic and aromatic compounds in the fluid sample.

When using spin echoes it is probably necessary to radiate RF directly at the frequency of where signals are expected, e.g. at 30 ppm from base carbon-13 resonance and in a second measurement at 130 ppm. Alternatively the interecho time needs to be specially chosen that the spin echo NMR resonance frequency, not identical with the transmitted RF frequency, has the correct phase relationship at the position of each RF pulse. Using NMR FIDs or CWNMR instead of spin echoes avoids this problem.

Figure 8A:
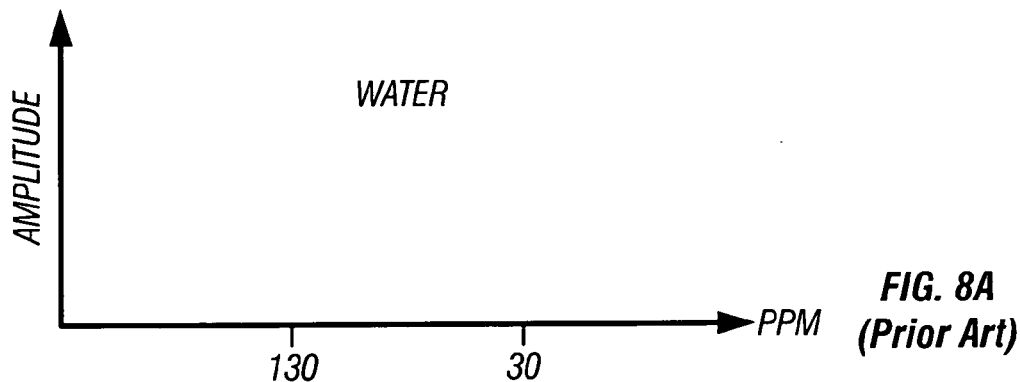
Figure 8B:
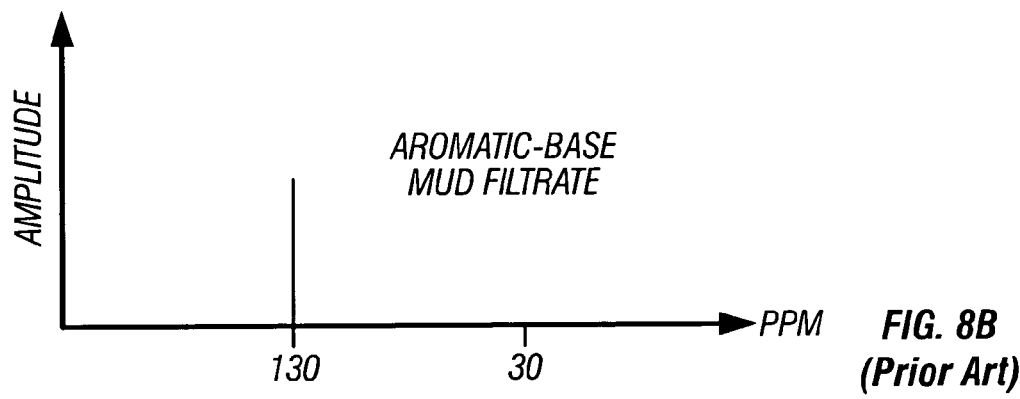
Figure 8C:
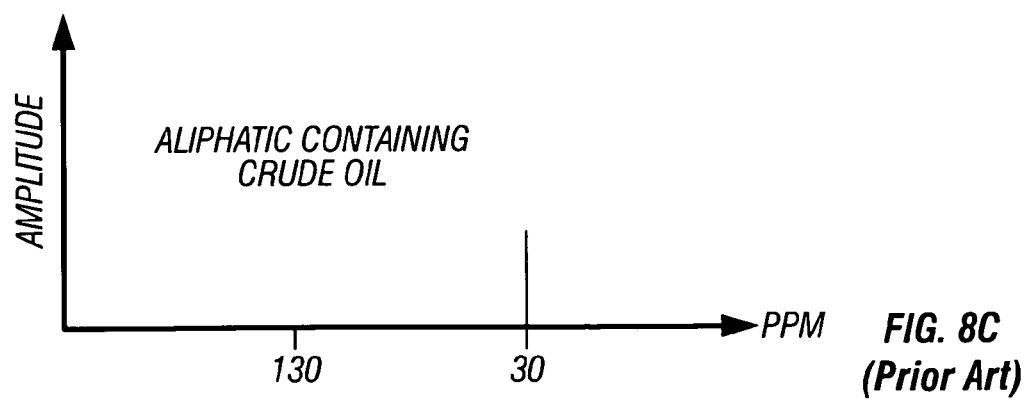

An example of analyses using the method of the invention is shown in graphs in FIGS. 8A-8C. FIG. 8 shows a typical analysis of a fluid sample comprised mainly of water. Neither the 130 ppm portion of the spectrum nor the 30 ppm portion have any appreciable amplitude. In FIG. 8B, the fluid analyzed contains a substantial portion of aromatic hydrocarbon, which can be inferred from the substantial amplitude at 130 ppm and the lack of appreciable amplitude at 30 ppm. This response is typical of oil-based mud filtrates comprised mainly of aromatic compounds. If the mud filtrate is comprised of aliphatic compounds as well, the analysis of the fluid samples may be improved by first introducing a sample of the mud filtrate to the sensor (10 in FIG. 2) and performing NMR analysis as described herein. The resulting analysis can be compared to analyses made of fluids withdrawn from the earth formation to determine the extent to which the fluid is comprised of mud filtrate. An analysis of typical crude oil sample containing both aliphatic compounds and some aromatic compounds is shown in FIG. 8C.

The discussion of $^{13}C$ spectroscopy is an example of a best mode of operation of the present invention. It is not meant as a limitation of the invention. By changing the operating frequency of the NMR apparatus, the quantities of various isotopes can be determined. The best isotopes for NMR measurements are $^1H$, $^{23}Na$, and $^{35}Cl$. Other isotopes that can be measured using the techniques of the present invention include $^{17}O$, $^{25}Mg$, $^{33}S$, $^{37}Cl$, and $^{39}K$. NMR properties of commonly occurring elements in oilfield fluids may be found in the Table below.

| NMR Properties of Elements Common in Oilfield Fluids | | | | |
|---|---|---|---|---|
| Isotope | Frequency/ Frequency ($^1H$) | Natural Abundance | NMR Sensitivity[1] | Net Sensitivity[2] |
| $^1H$ | 1 | 1.00 | 1 | 1 |
| $^{13}C$ | 0.251 | 0.011 | $1.59 \times 10^{-2}$ | $1.75 \times 10^{-4}$ |
| $^{17}O$ | 0.136 | $3.7 \times 10^{-4}$ | $2.91 \times 10^{-2}$ | $1.08 \times 10^{-5}$ |
| $^{23}Na$ | 0.264 | 1.00 | $9.25 \times 10^{-2}$ | $9.25 \times 10^{-2}$ |
| $^{25}Mg$ | 0.061 | 0.101 | $2.67 \times 10^{-3}$ | $2.7 \times 10^{-4}$ |
| $^{33}S$ | 0.076 | 0.0076 | $2.26 \times 10^{-3}$ | $1.72 \times 10^{-5}$ |
| $^{35}Cl$ | 0.098 | 0.755 | $4.70 \times 10^{-3}$ | $3.55 \times 10^{-3}$ |
| $^{37}Cl$ | 0.082 | 0.245 | $2.71 \times 10^{-3}$ | $6.63 \times 10^{-4}$ |
| $^{39}K$ | 0.047 | 0.931 | $5.08 \times 10^{-4}$ | $4.74 \times 10^{-4}$ |

[1]At 100% abundance, $^1H = 1$
[2]At natural abundance, $^1H = 1$

In an alternate embodiment of the invention, measurements of formation and fluid properties are made in situ, e.g., by modifying an apparatus such as that described in U.S. Pat. No. 6,348,792, issued to Beard et al., having the same assignee as the present invention, and the contents of which are incorporated herein by reference.

Standard methods are known in the prior art whereby in situ measurements of $T_1$ and $T_2$ distribution enable one to determine measurement parameters of the surrounding earth formation, such as, among others, the porosity of the earth formation, permeability, and bound volume irreducible.

Permeability estimation from NMR is generally obtained using empirical correlations to porosity and either a log-mean relaxation time or a NMR-derived ratio of Free/Bound Water. The bound water fraction is generally estimated from the inverted $T_2$ distribution using a sharp or gradational $T_2$ cutoff, based on the observation that smaller pores are associated with shorter relaxation times.

The faster NMR relaxation in smaller pores is caused by higher surface/volume ratios, causing more frequent interactions between the proton spins and the surroundings. The permeability of a porous medium is generally controlled by the pore throat size (capillary size), and for sandstone the pore throat size often correlates well with pore body size, which again is related to grain size. The sensitivity of the NMR measurement to surface/volume ratio is therefore useful in predicting permeability. Besides surface/volume ratio, the NMR relaxation rate depends on surface type (pore wall lithology), bulk fluid properties, and diffusion relaxation caused by external or internal magnetic gradients.

Figure 12:
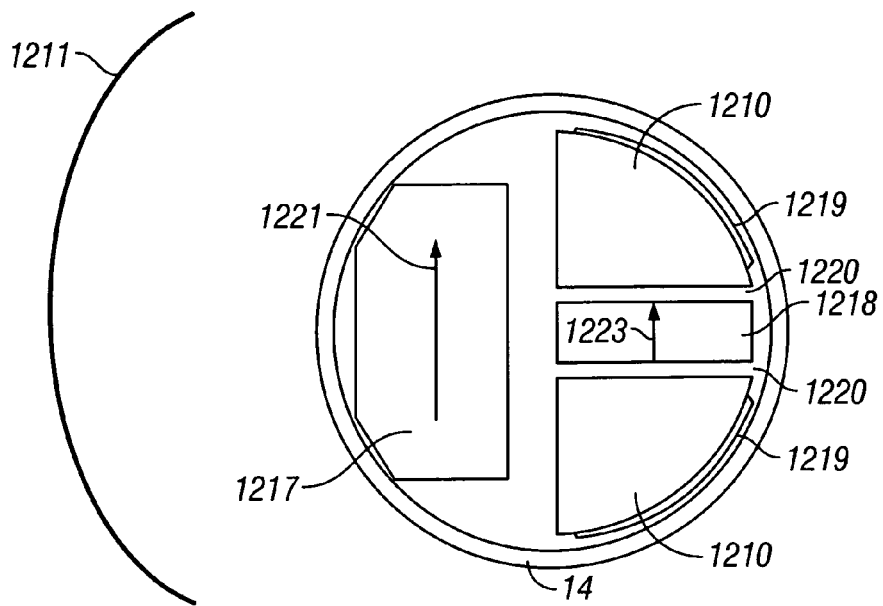

FIG. 12 schematically illustrates an embodiment of the present invention wherein the shaping of the static and RF fields is accomplished in a region within the earth formation. The tool cross-sectional view in FIG. 12 illustrates a main magnet 1217, a second magnet 1218, and a transceiver antenna, comprising wires 1219 and core material 1210. The arrows 1221 and 1223 depict the polarization (e.g., from the South pole to the North pole) of the main magnet 1217 and the secondary magnet 1218. A noteworthy feature of the arrangement shown in FIG. 12 is that the polarization of the magnets providing the static field is towards the side of the tool, rather than towards the front of the tool (the right side of FIG. 12).

The second magnet 1218 is positioned to augment the shape of the static magnetic field by adding a second magnetic dipole in close proximity to the RF dipole defined by the wires 1219 and the soft magnetic core 1210. This moves the center of the effective static dipole closer to the RF dipole, thereby increasing the azimuthal extent of the region of examination, the desirability of which has been discussed above. The second magnet 1218 also reduces the shunting effect of the high permeability magnetic core 1210 on the main magnet 1217: in the absence of the second magnet, the DC field would be effectively shorted by the core 1210. Thus, the second magnet, besides acting as a shaping magnet for shaping the static field to the front of the tool (the side of the main magnet) also acts as a bucking magnet with respect to the static field in the core 1210. Those versed in the art would recognize that the bucking function and a limited shaping could be accomplished simply by having a gap in the core; however, since some kind of field shaping is required on the front side of the tool, in an embodiment of the invention, the second magnet serves both for field shaping and for bucking. If the static field in the core 1210 is close to zero, then the magnetostrictive ringing from the core is substantially eliminated.

Figure 12A:
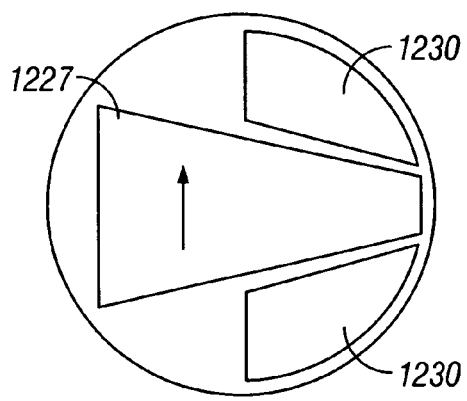
Figure 12B:
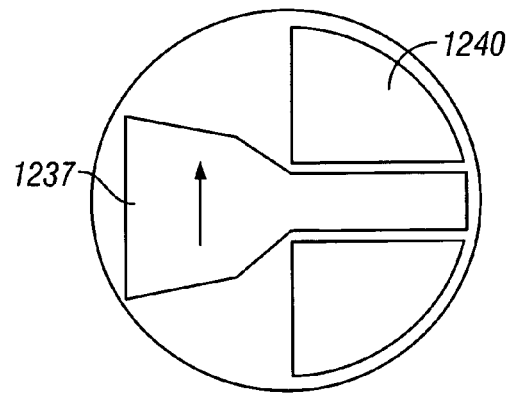

Within the region of investigation, the static field gradient is substantially uniform and the static field strength lies within predetermined limits to give a substantially uniform Larmor frequency. Those versed in the art would recognize that the combination of field shaping and bucking could be accomplished by other magnet configurations than those shown in FIG. 12. For example, FIG. 12A shows a single magnet 1227 and magnetic core 1230 that produces substantially the same static field as that produced by the combination of magnets 1217 and 1218 in FIG. 12. A substantially similar field configuration results from the arrangement in FIG. 12B with the magnet 1237 and the core 1240. What is being accomplished by the magnet arrangements in FIGS. 12, 12A and 12B is an asymmetry in the static magnetic field in a direction orthogonal to the direction of magnetization. In an optional embodiment of the invention (not shown) the second magnet is omitted.

Returning to FIG. 12, the transceiver wires 1219 and core pieces 1210 should be separated as far as possible towards the sides of the tool. This separation increases the transceiver antenna efficiency by increasing the effective RF dipole of the antenna and augments the shape of the RF magnetic field isolines so that they better conform to the static magnetic field isolines. The secondary magnet is made of a material such, as a nonconducting material, which minimizes eddy currents induced by the RF field, thereby increasing the RF antenna efficiency.

The NMR tool described above with reference to FIG. 12 is an example of a tool that may be used for determining formation properties. Many other suitable arrangements of magnets and antennae may be used. Those versed in the art would recognize that NMR sensors can utilize the earth magnetic field to perform a measurement. In this case no permanent magnets are required in the tool. It should also be noted that the invention may also be practice when the downhole tool is conveyed on a wireline.

While the foregoing disclosure is directed to the preferred embodiments of the invention, various modifications will be apparent to those skilled in the art. It is intended that all such variations within the scope and spirit of the appended claims be embraced by the foregoing disclosure.

What is claimed is:

1. A method of obtaining nuclear magnetic resonance signals from a fluid obtained from an earth formation, comprising:
    (a) conveying said fluid into a nuclear magnetic resonance (NMR) sensor in a borehole in said earth formation;
    (b) enhancing a polarization of a nuclear spin of a nucleus occurring in said fluid to a hyperpolarized state beyond that attainable for any atomic nucleus at thermal equilibrium in the applied magnetic field; and
    (c) using said NMR sensor for obtaining NMR signals from said fluid.

2. The method of claim 1 wherein enhancing said polarization of said nuclear spin is based at least in part on the Overhauser effect (OE).

3. The method of claim 1 wherein enhancing said polarization of said nuclear spin is based at least in part on the Nuclear Overhauser Effect (NOE).

4. The method of claim 1 wherein enhancing said polarization of said nuclear spin is based at least in part on optical pumping.

5. The method of claim 1 wherein enhancing said polarization of said nuclear spin is based at least in part on a Spin Induced Nuclear Overhauser Effect (SPINOE).

6. The method of claim 1 wherein enhancing said nuclear spin polarization further comprises:
    (i) introducing a polarizing agent into said fluid; and
    (ii) polarizing a spin of said polarizing agent, and
    (iii) transferring a polarization of said polarized agent to said nuclear spin.

7. The method of claim 1, further comprising conveying said sensor downhole on a wireline device.

8. The method of claim 1, further comprising conveying said sensor downhole on a measurement-while-drilling tool.

9. The method of claim 6, wherein said polarizing agent further comprises a noble gas.

10. The method of claim 9, wherein said polarizing agent further comprises xenon.

11. The method of claim 1, wherein said nucleus occurring in said fluid further comprises a carbon-13 nucleus present in at least one of: i) an aliphatic hydrocarbon, ii) an aromatic hydrocarbon, iii) a connate formation fluid, and, (iv) a mud filtrate.

12. The method of claim 6, wherein said polarizing said spin of said polarizing agent further comprises a spin exchange with an intermediate material.

13. The method of claim 12 wherein said intermediate material comprises rubidium.

14. The method of claim 12 further comprising irradiating said intermediate material with a laser to move electrons of said intermediate material to a higher quantum state.

15. The method of claim 1, wherein obtaining said nuclear magnetic resonance signal further comprises:
    i) providing a substantially homogeneous static magnetic field in a chamber containing said fluid;
    ii) applying a radio frequency pulse sequence to said fluid with at least one transmitter; and
    iii) obtaining NMR signals from said fluid in response to said radio frquency pulse sequence at at least one receiver antenna.

16. The method of claim 1 wherein obtaining said NMR signals further comprises obtaining spin echo signals.

17. The method of claim 16 further comprising:
    (i) summing amplitudes of said spin echo measurements;
    (ii) spectrally analyzing said summed amplitudes;
    (iii) determining whether aromatic hydrocarbons are present in said fluid sample by measuring an amplitude of said spectrally analyzed summed amplitudes at about 130 parts per million shift from a $^{13}$C resonant frequency and determining whether aliphatic hydrocarbons are present in said fluid sample by measuring an amplitude of said spectrally analyzed summed amplitudes at about 30 parts per million frequency shift from said $^{13}$C resonant frequency.

18. The method of claim 1 wherein said NMR signals comprise a free induction decay.

19. The method of claim 1 wherein said NMR signals are continuous wave NMR signals from which chemical shift information is obtained to analyze the chemical composition of the sample under test.

20. The method of claim 18 where the free induction decay is transformed into a frequency spectrum for analyzing chemical composition from the chemical shift information.

21. The method of claim 1 wherein said NMR signals are associated with a nuclear spin of $^{13}$C.

22. The method of claim 15 wherein said NMR signals are associated with a nuclear spin of $^{13}$C.

23. The method of claim 22 wherein providing said substantially homogeneous static magnetic field further comprises using additional NMR signals associated with $^1$H.

24. The method of claim 15 wherein providing said substantially homogeneous static magnetic field further comprises using additional NMR signals associated with $^1$H.

25. The method of claim 2 further comprising radiating RF into an Electron Spin Resonanace ESR-active agent at an ESR frequency of said agent and thereby enhancing the spin polarization of atomic nuclei.

26. The method of claim 3 further comprising changing a nuclear spin polarization of carbon-13 nuclei in said fluid by radiating RF at a NMR frequency of hydrogen nuclei.

27. An apparatus for use in a borehole in an earth formation for obtaining nuclear magnetic resonance signals from a fluid obtained from said formation, comprising:
(a) a nuclear magnetic resonance sensor;
(b) a device which enhances a polarization of a nuclear spin of a nucleus occurring in said fluid to a hyperpolarized state beyond that attainable for any atomic nucleus at thermal equilibrium in the applied magnetic field; and
(c) a processor which analyzes NMR signals obtained by said NMR sensor from said fluid.

28. The apparatus of claim 27 wherein said device for enhancing said polarization of said nuclear spin uses the Overhauser effect (OE).

29. The apparatus of claim 27 wherein said device for enhancing said polarization of said nuclear spin uses the Nuclear Overhauser Effect (NOE).

30. The apparatus of claim 27 wherein said device for enhancing said polarization of said nuclear spin uses optical pumping.

31. The apparatus of claim 27 wherein said device for enhancing said polarization of said nuclear spin uses a Spin Induced Nuclear Overhauser Effect (SPINOE).

32. The apparatus of claim 27 wherein said device for enhancing said nuclear spin further comprises:
(i) an arrangement for introducing a polarizing agent into said fluid; and
(ii) an arrangement for polarizing a spin of said polarizing agent.

33. The apparatus of claim 32, wherein said polarizing agent further comprises a noble gas.

34. The apparatus of claim 33, wherein said polarizing agent further comprises xenon.

35. The apparatus of claim 27, wherein said nucleus occurring in said fluid further comprises a carbon-13 nucleus present in at least one of: i) an aliphatic hydrocarbon, ii) an aromatic hydrocarbon, iii) a connate formation fluid, and, (iv) a mud filtrate.

36. The apparatus of claim 32, wherein said polarizing said spin of said polarizing agent further comprises a spin exchange with an intermediate material.

37. The apparatus of claim 36 wherein said intermediate material comprises rubidium.

38. The apparatus of claim 36 further comprising a laser which moves electrons from the S to the P quantum state of said intermediate material.

39. The apparatus of claim 27, further comprising:
i) a fluid chamber;
ii) a magnet arrangement which provides a substantially homogeneous static magnetic field in said chamber;
iii) a transmitter which applies a radio frequency magnetic field to said fluid;
iv) a receiver which obtains NMR signals from said fluid in response to said radio frequency magnetic field.

40. The apparatus of claim 27 wherein said NMR signals further comprise obtaining spin echo signals.

41. The apparatus of claim 40 further comprising:
a processor which:
(i) sums amplitudes of said spin echo measurements;
(ii) spectrally analyzes said summed amplitudes; and
(iii) determines whether aromatic hydrocarbons are present in said fluid sample by measuring an amplitude of said spectrally analyzed summed amplitudes at a first frequency shift from a $^{13}$C resonant frequency and determining whether aliphatic hydrocarbons are present in said fluid sample by measuring an amplitude of said spectrally analyzed summed amplitudes at a second frequency shift from said $^{13}$C resonant frequency.

42. The apparatus of claim 27 wherein said NMR signals comprise a free induction decay.

43. The apparatus of claim 42 where said processor transforms the free induction decay into a frequency spectrum for analyzing chemical composition from the chemical shift information.

44. The apparatus of claim 27 where said NMR signals comprise a CW frequency spectrum.

45. The apparatus of claim 27 wherein said NMR signals are associated with a nuclear spin of $^{13}$C.

46. The apparatus of claim 38 wherein said NMR signals are associated with a nuclear spin of $^{13}$C.

47. The apparatus of claim 28 wherein said NMR sensor includes a transmitter that applies an RF magnetic field to said fluid at an electron spin resonance (ESR) frequency of an ESR-active agent 48. The apparatus of claim 29 wherein said NMR sensor includes a transmitter that applies an RF magnetic field to said fluid at nuclear resonance frequency of hydrogen nuclei in said fluid.

49. A system for obtaining nuclear magnetic resonance signals from a fluid obtained from a fluid obtained from an earth formation, comprising:
(a) a logging tool including a nuclear magnetic resonance (NMR) sensor;
(b) a first conveyance device which conveys said fluid into a chamber of said (NMR) sensor;
(c) an arrangement which enhances a polarization of a nuclear spin of a nucleus occurring in said fluid to a hyperpolarized state beyond that attainable for any atomic nucleus at thermal equilibrium in the applied magnetic field;

(d) a processor which determines from signals obtained by said NMR sensor a property of said fluid; and (e) a conveyance device which conveys said logging tool into said earth formation.

50. The system of claim 49 wherein said conveyance device is selected from the group consisting of (i) a wireline, and, (ii) a drilling tubular, and, (iii) coiled tubing.

51. The system of claim 49 wherein said arrangement in (c) uses at least one of (i) the Overhauser Effect (OE), (ii) the Nuclear Overhauser Effect (NOE), (iii) optical pumping or (iv) Spin Polarization Induced Nuclear Overhauser Effect (SPINOE).

52. The system of claim 49 wherein said arrangement in (c) uses at least one of (i) a noble gas, (ii) xenon, (iii) an alkaline metal, and, (iv) rubidium.

53. The system of claim 49 further comprising a laser optically pumps at least of one of (i) a noble gas, and, (ii) xenon.

* * * * *